Figure 1:
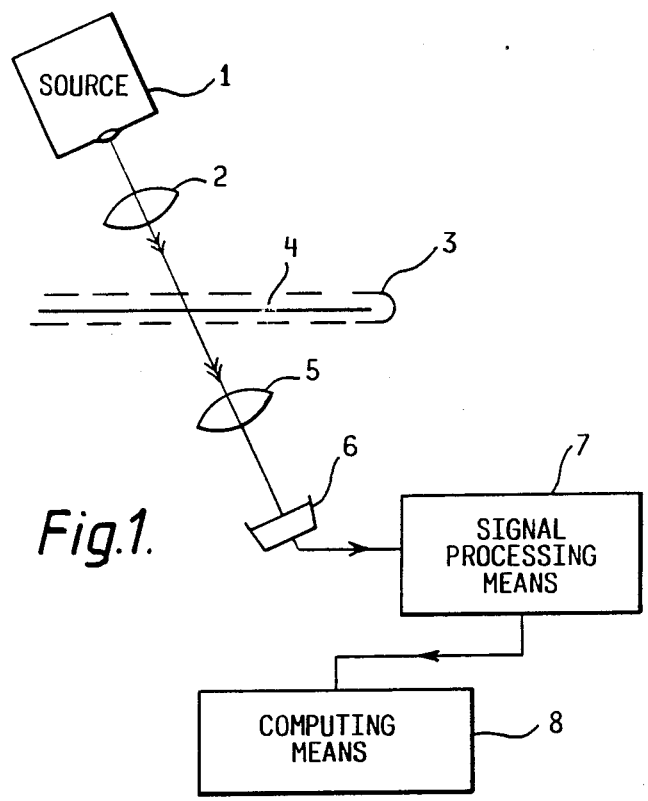

United States Patent [19]

Edgar

[11] Patent Number: 4,952,061
[45] Date of Patent: Aug. 28, 1990

[54] METHOD AND APPARATUS FOR SENSING OR DETERMINING ONE OR MORE PROPERTIES OR THE IDENTITY OF A SAMPLE

[75] Inventor: Rodger F. Edgar, Maldon, England
[73] Assignee: Infrared Engineering Limited, England
[21] Appl. No.: 211,708
[22] Filed: Jun. 27, 1988
[30] Foreign Application Priority Data
Jul. 2, 1987 [GB] United Kingdom ............ 8715608
[51] Int. Cl.⁵ ............ G01B 11/02; G01N 21/27
[52] U.S. Cl. ............ 356/407; 356/320; 356/381; 356/382; 356/433; 356/448; 364/563; 364/728.03
[58] Field of Search ............ 356/320, 381, 382, 407, 356/432, 433, 445, 446, 448; 364/563, 728.03
[56] References Cited
U.S. PATENT DOCUMENTS
4,555,767  11/1985  Case et al. ............ 356/381

Primary Examiner—F. L. Evans
Attorney, Agent, or Firm—Leydig, Voit & Mayer

[57] ABSTRACT

In a method wherein sets of measured values of the intensity of electromagnetic radiation, which has been subject to optical interference, absorption or scatter by a sample, are correlated with different sets of known values derived from either a model of the optical properties of the sample, or from an analogue technique, correlation is by means of either a zero dependent correlation function, or a normalized residual function. Both functions are unaffected by gain factors, thereby avoiding any need to determine and to maintain absolute sensitivities of optical detectors; provide greater variation of correlation than with techniques employing a conventional correlation coefficient, thereby increasing the precision with which the optimum correlation can be determined, especially when either the measured value, or known values are subject to error; enable the method to be carried out with only two radiation components; and can enable a reduction in computing time.

4 Claims, 2 Drawing Sheets

METHOD AND APPARATUS FOR SENSING OR DETERMINING ONE OR MORE PROPERTIES OR THE IDENTITY OF A SAMPLE

This invention relates to an improvement to methods and apparatus for sensing or determining one or more properties, or the identity of a sample in which electromagnetic radiation is subject to optical interference, absorption or scatter.

In our previous European Patent Application No. 87300251.3 and corresponding U.S. application No. 0047347 (filed 16 th Jan. 1987) there are disclosed methods wherein sets of measured values of the intensity of electromagnetic radiation which has been subject to optical interference, absorption or scatter by a sample are correlated with different sets of known values derived from either a model of the optical properties of the sample, or by an analogue technique.

In the case of using a model, the model predicts values for the intensities of sets of radiation components of differing spectral properties as a function of the property or identity of the sample which is to be determined. Differing values of the property, or properties, or different identities, are applied to the model to predict the different sets of known values.

European Patent Application No. 87300251.3 teaches the use of correlation coefficient, as customarily defined in statistics, as a means of selecting the set of known values which provides the closest agreement with the set of measured intensity values. Selection of the set of known values which has an optimum correlation with the set or sets of measured intensity values enables the property or properties (such as thickness) to be sensed or the identity to be determined.

It might be expected that a maximum correlation coefficient would be required, but European Patent Application No. 87300251.3 also teaches ways in which the model used to predict the known values may be modified so as to permit other values of correlation coefficient to be optimum. In particular, by using a model based on differential values of transmittance or reflectance of the sample, it is sometimes possible for a zero correlation value to be optimum. Since the zero values represent a transition between a positive and a negative value the value of the determining property can be estimated by linear interpolation between a local overestimate and a local underestimate. This is a simpler process than determining the position of a maximum from local incorrect estimates.

U.S. Pat. No. 4,555,767 describes a method in which the thickness of an epitaxial layer on a sample is determined from the correlation between a set of measured intensity values of electromagnetic radiation over a continuous spectral region reflected from the sample and different sets of known values derived from a model.

This method is more restricted than those of European Patent Application No. 873000251.3 which teaches methods of selecting small sets of values rather than requiring correlation over a continuous spectral region.

The use of the conventional correlation coefficient has the advantage that it renders the correlation coefficient insensitive to uncertainty or errors in estimating the zero level of the set of measured intensity values. It further renders the result insensitive to uncertainty as to any gain or sensitivity factor that affect the set of measured intensity values.

Similarly, the customary way in which correlation coefficient is defined provides an equivalent insensitivity to zero level or gain factors in the sets of known values when derived from a model.

These are useful practical benefits since firstly, relative measurements may be easier to carry out than absolute measurements, and secondly, simplified models may on occasions be used.

These two benefits are evident when measuring, for example, optically flat, thin films, where optical interference effects may predominate over absorption or scatter.

In certain circumstances where optical absorption or scatter effects are more important, these benefits may be less important and correlation coefficient suffers from an important disadvantage. For the method to be effective, the correlation coefficient between measured and known values must change appreciably with the changes in the set of known values arising as the property or identity to be determined is varied.

Without such appreciable changes it becomes very difficult to determine the optimum, especially in the presence of slight errors in the measured values. Further, when correlation coefficient is used, each set of known values must have at least three members (i.e. corresponding with at least three components of radiation to be transmitted through, or reflected from the sample). Further, when a model is used, the model must predict relatively different values for all three members in each set.

For example, in a case where the method was used by selecting spectral regions in the vicinity of an optical absorption band, it would not be possible to use a wavelength region centered on the absorption band together with two regions of negligible absorption at slightly shorter and longer wavelengths respectively, since the absorption characteristics of the latter would not be sufficiently different.

This invention seeks to provide an improvement in the method and overcome these disadvantages by calculating a new correlation function in accordance with the formula.

$$s = \frac{\sum_{i=1}^{n} x_i y_i}{\left( \sum_{i=1}^{n} x_i^2 \sum_{i=1}^{n} y_i^2 \right)^{\frac{1}{2}}} \tag{1}$$

where $x_i$ and $y_i$ represent sets of measured and known values, each set comprising n members.

Alternatively the improvement may be effected by calculating a new residual function in accordance with the formula:

$$Nres = \sum_{i=1}^{n} \left( \frac{x_i}{\left( \sum_{i=1}^{n} x_i^2 \right)^{\frac{1}{2}}} - \frac{y_i}{\left( \sum_{i=1}^{n} y_i^2 \right)^{\frac{1}{2}}} \right)^2 \tag{2}$$

It will be shown that these two formulae are closely related and can provide identical results.

A characteristic of the first formula is that, unlike the convention correlation coefficient, the new correlation function is sensitive to the zero level of the measured values (and also of a model when used). Hence it will be described as the zero dependent correlation function.

The residual function in equation (2) has in effect been normalised, but is also affected by the zero level of both measured and model values. It will be described as a normalised residual function.

Neither zero dependent correlation function nor normalised residual function is affected by constant gain factors affecting all members of the set equally.

According to this invention, a method of sensing or determining one or more properties or the identity of a sample in which electromagnetic radiation is subject to optical interference, absorption or scatter, comprises the steps of:

(a) causing electromagnetic radiation to be transmitted through, or reflected from said sample, said radiation including at least two spectrally different components so that at least one of said components is subjected to said optical interference, absorption or scatter and so that said components are transmitted through, or reflected from said sample by respectively different amounts;

(b) measuring the transmittance or reflectance of said sample for each of said components to derive respective measured values;

(c) correlating by means of either a zero dependent correlation function, or a residual function respectively defined by:

$$s = \frac{\sum_{i=1}^{n} x_i y_i}{\left(\sum_{i=1}^{n} x_i^2 \cdot \sum_{i=1}^{n} y_i^2\right)^{\frac{1}{2}}}$$

$$Nres = \sum_{i=1}^{n} \left(\frac{x_i}{\left(\sum_{i=1}^{n} x_i^2\right)^{\frac{1}{2}}} - \frac{y_i}{\left(\sum_{i=1}^{n} y_i^2\right)^{\frac{1}{2}}}\right)^2$$

said measured values of transmittance or reflectance with different known values representing or relating to either different values of a property of a known material, or different values which are characteristic of different known materials: and (d) selecting the known values having an optimum correlation with said measured values, the selected known values representing the property, or the identity of the sample which is sensed or to be determined.

Known optical and electronic apparatus, capable of causing electromagnetic radiation to be transmitted through, or reflected from the sample and of measuring the transmittance or reflectance of the sample for each of the radiation components, can be used to generate the measured values. One practical embodiment of this invention employs such apparatus to generate the measured values and these are fed into a computer which is programmed to carry out the steps of (a) predicting sets of the known values from a mathematical model or models; (b) correlating sets of the known and the measured values using either the zero dependent correlation function, or the residual function; and (c) selecting the magnitude of the property or identity of the sample that generates the optimum correlation. The predicted known values may be derived by applying to the mathematical model, or models (i) known values relating to the properties of the radiation components, and (ii) different magnitudes of the property to be sensed or determined; said model or models taking account of absorption, and/or interference, and/or scatter (preferably both absorption and interference where this is appropriate). However, instead of using a model or models to predict the known values, the known values may be derived by an analogue technique wherein the electromagnetic radiation is transmitted through, or reflected from either a material similar to the sample and having different known magnitudes of the property to be sensed or determined, or different known materials having different known magnitudes of the property to be sensed or determined.

Figure 2:
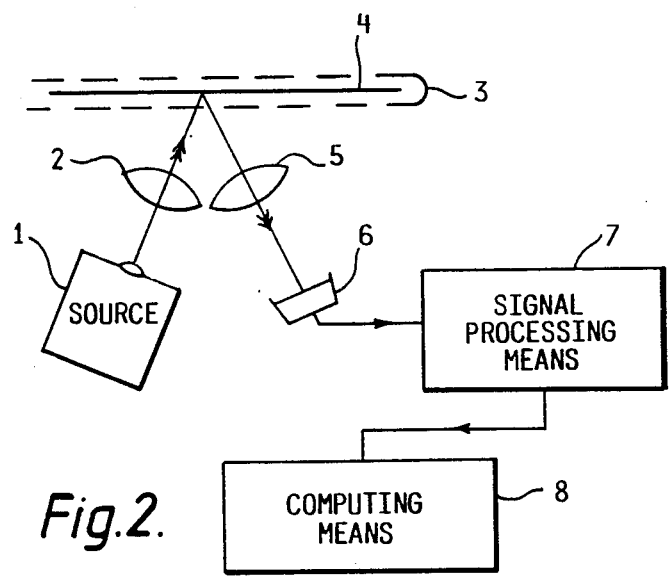
Figure 3:
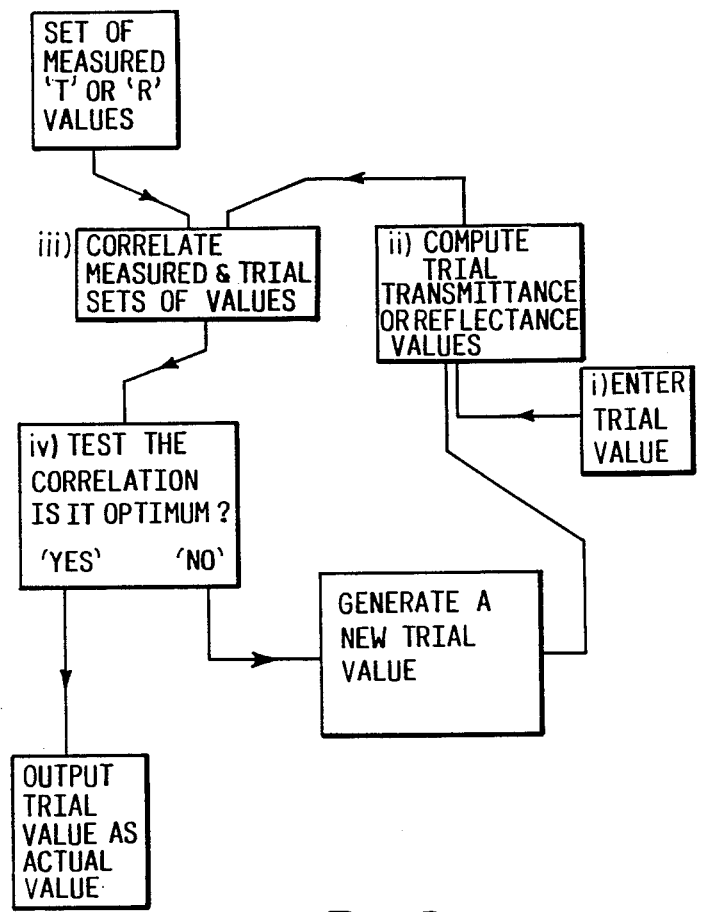

Embodiments of the invention will now be described with reference to the accompanying drawings, in which:

FIG. 1 illustrates optical, electronic and computing apparatus according to one embodiment of the invention, for making measurements using transmission of radiation through a sample, FIG. 2 illustrates optical, electronic and computing apparatus according to another embodiment of the invention, for making measurements using the reflection of radiation by a sample, and FIG. 3 shows schematically the computing steps involved in determining a property or identity of a sample, starting from the set of measured values.

Referring to FIG. 1 which shows apparatus operating by transmission through a sample according to an embodiment of this invention, a number of beams of radiation including two or more of different spectral composition are generated by source, 1, and directed by first optical directing means, 2, into sample zone, 3, so that they impinge upon sample, 4, at a defined angle of incidence. A fraction of each of said beams which is transmitted by sample, 4, is then directed by second optical directing means, 5, onto detector means 6. The signals produced by detector means, 6, which represent the several intensities of those fractions of each of said beams which is transmitted by sample, 4, are amplified and demodulated if necessary by signal processing means, 7, and transmitted to computing means, 8, which computes the magnitude of the property or identity of the sample, 4, that is to be determined, by means and methods that will be described later.

Referring to FIG. 2 which shows apparatus operating by reflection from a sample, according to an embodiment of this invention, a number of beams of radiation including two or more of different spectral composition are generated by source, 1, and directed by first optical directing means, 2, into sample zone, 3, so that they impinge upon sample, 4, at a defined angle of incidence. A fraction of each of said beams which is reflected by sample, 4, is then directed by second optical directing means, 5, onto detector means, 6. The signals produced by detector means, 6, which represent the several intensities of those fractions of each of said beams which is reflected by sample, 4, are amplified and demodulated if necessary by signal processing means, 7, and transmitted to computing means, 8, which compute the magnitude of the property or identity of the sample 4, that is to be determined, by means and methods that will be described later.

Source means capable of producing the two or more beams of different spectral composition are known in the prior art. Examples include both spectrally tuneable and fixed wavelength lasers and light emitting diodes. If the source means includes more than one source, precise optical alignment will be needed to ensure that the several light beams are projected onto the same area of the sample at the same angle. Commonly the source means will comprise a filament lamp or other spectrally broadband source used in collaboration with some filter means. Optical interference filters are a suitable filter means, but it will also be apparent to persons skilled in the art that prisms, diffraction gratings, zone plates etcetera could be used.

It will also be obvious to persons skilled in the art that when a spectrally broadband source is used, the precise location of the optical filter means in the light path from source to detector is not critical.

Indeed, it may be more convenient to illuminate the sample with a broadband source and only select the spectrally different beams after the light has been transmitted or reflected by the sample.

The first and second optical directing means are optical elements, or combinations thereof that are well known in the prior art, including lenses, mirrors, prisms optical fibres etcetera. In some cases one optical element or combination may be made to serve as first and second optical directing means, and in the case of some systems using a laser or lasers as source, the optical system of the laser or, lasers in effect may provide either the first, or the first and second optical directing means.

The detector means may include one or more detectors. If the number of detectors is less than the number of light beams, then some means of presenting two or more beams to at least one of the detectors must be utilised. Such means could include sequential presentation (for example, by means of a rotating filter wheel) or the modulation of each beam at a different frequency, with a corresponding demodulation of the detector signal. In the event of sequential presentation being used, all beams must be presented in a time which is so short that the optical path within the sample will not have changed during the sequence. Especially for on-line measurement, this is fairly demanding requirement and apparatus permitting simultaneous measurement of the beams may be preferred.

Where a multiplicity of detectors is adopted it may prove beneficial to provide for adjustment or correction for the relative sensitivities of the detectors for example, after measuring the detector signals in the absence of a sample, or in the presence of a known sample or both.

The apparatus may be designed to function with a wide range of types of detector. The choice of detector will depend upon the spectral region over which the apparatus is to operate, upon the desired response speed of the measurement and will present few difficulties to those skilled in the art. Detectors which could be used include photomultiplier tubes, silicon or germanium photodiodes or arrays thereof such as charge-coupled-devices, photoconductive and photovoltaic semiconductors, and thermal detectors such as thermocouples or pyroelectric detectors or arrays thereof.

The signal processing means may use known electronic means to amplify the signal or signals so as to produce the set of signals which represent the transmission or reflection of the sample for each of the light beams used. If adjustment or correction for the relative sensitivities of the detectors is required it may be applied at this stage or it may be applied as part of the subsequent computing means.

In FIG. 3 is shown one possible sequence of computing steps by which a property or identity of a sample may be determined.

Film thickness is described by way of an example.

(i) The computing sequence may commence with the entry of a trial thickness value. Such a trial thickness value could be determined by some other measuring means, or entered manually by an operator or a previous measured thickness value could be automatically used as the current trial thickness value.

(ii) Using a model a set of trial transmittance or reflectance values is computed, based on the application of the model to the trial thickness value. The model will be based upon an equation or a set of equations describing the way in which electromagnetic radiation interacts with the sample equations. Examples of possible equations are the Beer-Lambert absorption law and the Kubelka-Munk scattering equations, which are well known in optics.

(iii) Using the zero dependent correlation function a correlation between measured and trial transmittance or reflectance values is computed.

(iv) The correlation is tested to determined whether or not it is an optimum. If it is, then the trial thickness value is adopted as the measured thickness value. If the correlation is not an optimum, then a new trial thickness value is generated and steps (ii), (iii) and (iv) are repeated until an optimum correlation is obtained. In general it will be necessary to complete several sets of trial values before an optimum is derived.

Various strategies may be used to compute new trial thickness values from existing ones and their associated correlations. The several strategies taught in European Patent Application No. 87300251.3 will be equally effective with both the conventional and the new zero dependent correlation functions. EPA No. 87300251.3 also teaches methods of selection of groups of measurement wavelengths and computing strategies to cope with correlation functions having multiple maxima or minima, as may arise when the invention is used to determine the thickness of thin, optically flat films.

The new, zero dependent correlation function may be used in conjunction with these strategies.

U.S. Pat. No. 4555767 teaches a means of determining the trial thickness that yields a maximum correlation by statistically fitting a parabolic curve to correlation values associated with near estimates. Again, the new zero dependent correlation function may be used with this strategy and will give improved results in many cases.

Where the invention is used to determine an identity, the computing sequences described above may not be necessary. The usual method will be to compare the measured values with sets of trial values relating to each of the possible identities and select the one which generates the optimum correlation.

With modern digital computing means the repetitive and possibly time variable element in the computation is not a serious disadvantage, and the computation can be carried out in less than 0.1 second, permitting an essentially continuous measurement to be made during, for example, a production process.

In understanding the advantages of this invention it is helpful to note the relationships between conventional correlation coefficient, the new, zero dependent correlation function and the new normalised residual function.

For two sets of data, each consisting of n points, such as a set of measured values $x_1$ and a set of known values $y_1$ the conventional correlation coefficient is defined by:

$$r = \frac{\sum_{i=1}^{n}(x_i - \bar{x})(y_i - \bar{y})}{\left(\sum_{i=1}^{n}(x_i - \bar{x})^2 \sum_{i=1}^{n}(y_i - \bar{y})^2\right)^{\frac{1}{2}}} \quad (3)$$

where $\bar{x}$ and $\bar{y}$ are mean values defined by the equations:

$$\bar{y} = \frac{1}{n} \sum_{i=1}^{n} y_i \quad (4)$$

$$\bar{x} = \frac{1}{n} \sum_{i=1}^{n} x_i \quad (5)$$

The new, zero dependent correlation function that is used in this invention is defined by:

$$s = \frac{\sum_{i=1}^{n} x_i y_i}{\left(\sum_{i=1}^{n} x_i^2 \cdot \sum_{i=1}^{n} y_i^2\right)^{\frac{1}{2}}} \quad (6)$$

The residual between the two data sets is conventionally defined by:

$$Res = \Sigma(X_i - y_i)^2 \quad (7)$$

The new, normalised, residual function that may be used in this invention is defined by:

$$Nres = \sum_{i=1}^{n} \left( \frac{x_i}{\left(\sum_{i=1}^{n} x_i^2\right)^{\frac{1}{2}}} - \frac{y_i}{\left(\sum_{i=1}^{n} y_i^2\right)^{\frac{1}{2}}} \right)^2 \quad (2)$$

This may be expanded out and becomes $$N_{res} = 2 - 2 \frac{\sum_{i=1}^{n} x_i y_i}{\left(\sum_{i=1}^{n} x_i^2 \sum_{i=1}^{n} y_i^2\right)^{\frac{1}{2}}} \quad (8)$$

Hence $$Nres = 2(1 - s) \quad (9)$$

Given this clear and simple relationship between the new correlation function s and the normalised residual function Nres, it is obvious that the invention may be implemented using either.

The following sample data helps to understand the differences between conventional and new correlation and residual functions.

Data set $x_i$ (used for all 3 examples)
$x_1 = 1 \; x_2 = 2 \; x_3 = 3 \; x_4 = 4 \; x_5 = 5$ Data set $y_i$ (identical values to $x_i$)
$y_1 = 1 \; y_2 = 2 \; y_3 = 3 \; y_4 = 4 \; y_5 = 5$
$r = 1 \; s = 1 \; Res = 0 \; Nres = 0$ Data set $y_i$ (= $x_i$ multiplied by a constant)
$y_1 = 2 \; y_2 = 4 \; y_3 = 6 \; y_4 = 8 \; y_5 = 10$
$r = 1 \; s = 1 Res = 55 \; Nres = 0$ -continued Data set $y_i$ (= $x_i$ plus a constant)
$y_1 = 5 \; y_2 = 6 \; y_3 = 7 \; Y_4 = 8 \; y_5 = 9$
$r = 1 \; s = 0.9711 \; Res = 80 \; Nres = 0.0578$ It can be seen that the conventional correlation coefficient (r above) is insensitive to both zero errors (adding a constant) and gain factors (multiplying by a constant). The residual is sensitive to both.

Both the new zero dependent correlation (s above) and the new normalised residual are sensitive to zero errors but unaffected by gain factors. This is very useful when zero levels of signals can be established with certainty but absolute gains cannot. This is common with detectors which are sensitive to optical radiation.

It is obvious that the new correlation function s, in common with the conventional correlation coefficient, can only have values between $-1$ and $+1$ and from equation (9) the new normalised residual can only have values between 4 and 0.

It is further obvious that any value of the new correlation function s has a corresponding value of the new normalised residual Nres. Thus any optimisation of Nres may be considered as an optimisation of s. Therefore any description of the method and apparatus in terms of the new zero dependent correlation will be understood to encompass the new normalised residual.

The advantage of using the new correlation function may be summarised as follows.

The amount of computation required can be reduced.

It provides a greater variation of correlation as a function of different sets of known values. This increases the precision with which the optimum correlation can be determined, especially when either the measured values, or known values are subject to error.

A further benefit is that it permits the method to operate when each set of known values has as few as two members, whereas the conventional correlation coefficient is defined for sets of known values each having three or more members with relatively different values (since if it were computed, according to equation (3) above, with only two members in each set, it would always give a value of 1).

It is often convenient in measurements involving optical absorption bands, to use a set of three wavelength regions, one centered on the absorption band, and the other two at wavelengths long and short of the band of which the absorption is negligible. Because the absorption of the long and short wavelength bands is very similar, they behave almost like a single band and again, the conventional correlation coefficient will give results very close to 1 in this case, regardless of the known values which are used. The new zero dependent correlation coefficient does not suffer from this limitation, and can give sensible results with either two radiation components or with three of which two are affected identically by the sample.

Whilst it is necessary to avoid zero errors in the measured values, the method still permits variations in absolute gain or sensitivity, which is very desirable in any optical instrument, since it is hard to determine and maintain absolute sensitivities of optical detectors.

The new zero dependent correlation may be applied to measurements in which measured values from complete spectra are correlated with known values of complete spectra, or it may be applied to sets of measured values and known values representing discrete radiation components, such as isolated wavebands selected from a broad spectral region. Such selection allows simpler and more rapid computing and lower cost, especially where the number of radiation components can be reduced to two.

Whilst preferred embodiments of the invention have been described above, changes and modifications may be made without departing from the scope of the invention.

I claim:

1. A method of sensing or determining one or more properties or the identity of a sample in which electromagnetic radiation is subject to optical interference, absorption or scatter, the method comprising the steps of:
   (a) causing electromagnetic radiation to be transmitted through, or reflected from said sample, said radiation including at least two spectrally different components so that at least one of said components is subjected to said optical interference, absorption or scatter and so that said components are transmitted through, or reflected from said sample by respectively different amounts;
   (b) measuring the transmittance or reflectance of said sample for each of said components to derive respective measured values;
   (c) correlating by means of either a zero dependent correlation function 'S', or a residual function 'Nres', respectively defined by:

$$S = \frac{\sum_{i=1}^{n} x_i y_i}{\left(\sum_{i=1}^{n} x_i^2 \cdot \sum_{i=1}^{n} y_i^2\right)^{\frac{1}{2}}}$$

where:
i is an integer,
n is an integer representing a number of data points,
$x_i$ represents a set of said measured data values at respective data points,
$y_i$ represents a set of known data values at the same data points $$Nres = \sum_{i=1}^{n} \left(\frac{x_i}{\left(\sum_{i=1}^{n} x_i^2\right)^{\frac{1}{2}}} - \frac{y_i}{\left(\sum_{i=1}^{n} y_i^2\right)^{\frac{1}{2}}}\right)^2$$

said measured values of transmittance or reflectance with different known values representing or relating to either different values of a property of a known material, or different values which are characteristic of different known materials; and
   (d) selecting the known values having an optimum correlation with said measured values, the selected known values representing the property, or the identity of the sample which is sensed or to be determined.

2. A method according to claim 1 wherein said known values are derived by applying to a mathematical model, or models, (i) known values relating to the properties of the radiation components, and (ii) different magnitudes of the property to be sensed or determined; said model or models taking account of absorption, and/or interference, and/or scatter.

3. A method according to claim 1 wherein said known values are derived by an analogue technique wherein the electromagnetic radiation is transmitted through, or reflected from either a material similar to the sample and having different known magnitudes of the property to be sensed or determined, or different known materials having different known magnitudes of the property to be sensed or determined.

4. Apparatus for sensing or determining one or more properties or the identity of a sample in which electromagnetic radiation is subject to optical interference, absorption, or scatter the apparatus comprising:
   (a) means for causing electromagnetic radiation to be transmitted through, or reflected from said sample, said radiation including at least two spectrally different components so that at least one of said components is subjected to said optical interference, absorption, or scatter and so that said components are transmitted through, or reflected from said sample by respectively different amounts;
   (b) means for receiving said transmitted or reflected radiation components and for providing corresponding measurement values;
   (c) means for providing different known values of transmittance or reflectance, and different known values representing or relating to either different values of a property of a known material, or different characteristics of different materials, or both; and
   (d) means for determining the correlation between said measured values and said known values and for selecting the known values having an optimum correlation with said measured values, the selected known values representing the property, or the identity of the sample which is sensed or to be determined, the latter means determining said correlation by either a zero dependent correlation function, or a residual function which are respectively defined by:

$$S = \frac{\sum_{i=1}^{n} x_i y_i}{\left(\sum_{i=1}^{n} x_i^2 \cdot \sum_{i=1}^{n} y_i^2\right)^{\frac{1}{2}}}$$

where:
i is an integer,
n is an integer representing a number of data points,
$x_i$ represents a set of said measured data values at respective data points,
$y_i$ represents a set of known data values at the same data points $$Nres = \sum_{i=1}^{n} \left(\frac{x_i}{\left(\sum_{i=1}^{n} x_i^2\right)^{\frac{1}{2}}} - \frac{y_i}{\left(\sum_{i=1}^{n} y_i^2\right)^{\frac{1}{2}}}\right)^2$$

* * * * *